United States Patent [19]

Craig et al.

[11] Patent Number: Plant 7,343

[45] Date of Patent: Oct. 2, 1990

[54] REGAL PELARGONIUM 'CRYSTAL'

[75] Inventors: Richard Craig, State College, Pa.; Glenn G. Hanniford, Worthington, Ohio

[73] Assignee: Research Corporation Technologies, Inc., Tucson, Ariz.

[21] Appl. No.: 337,782

[22] Filed: Apr. 10, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Scully, Scott, Murphy & Presser

[57] ABSTRACT

This invention relates to a new and distinct cultivar of regal pelargonium (*Pelargonium*×*domesticum*) named 'Crystal' substantially as illustrated and described herein, particularly characterized as being compact and self-branching, early flowering and floriferous, exhibiting excellent postharvest keeping quality, and having white flowers with distinctive red feathering on the upper two petals thereof.

2 Drawing Sheets

The present invention relates to a new and distinct cultivar of regal pelargonium (*Pelargonium*×*domesticum*) called 'Crystal'. This cultivar is very compact and self-branching (without pinching), early flowering and floriferous, with excellent postharvest keeping quality. The flowers are pure white with distinctive red feathering on the upper two petals.

The cultivar was developed from an organized, scientifically designed breeding program conducted at the Department of Horticulture. The Pennsylvania State University, University Park, Pa. 16802. The objective was to produce a new regal pelargonium genotype with excellent propagation characteristics, compact growth habit, predictable and consistent flowering response, and excellent postharvest quality. 'Crystal' resulted from the selection from the progeny of the self-pollination of regal pelargonium cultivar 'Virginia'. The selection was asexually propagated by cuttings and the reproductions ran true.

Figure 1:
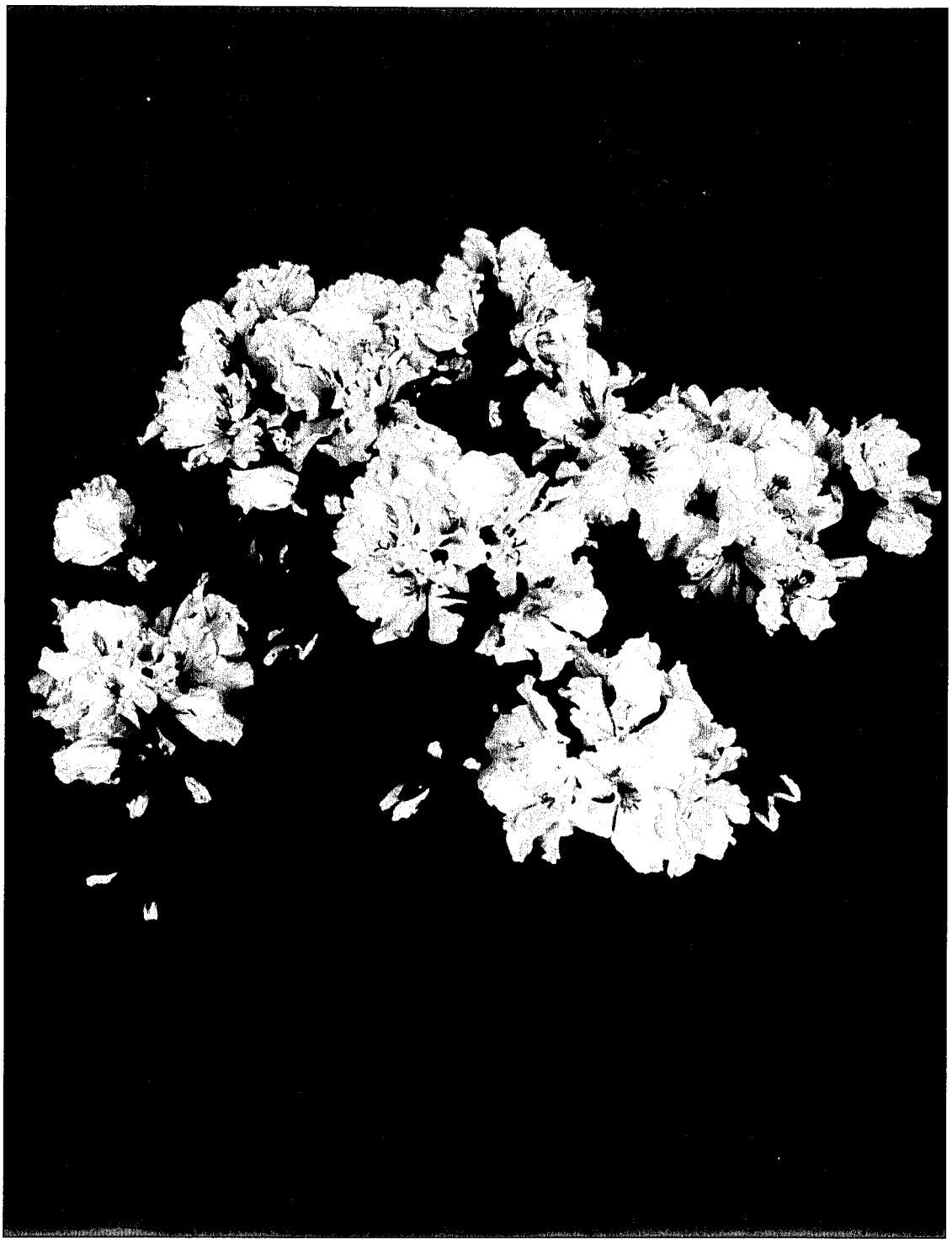
FIG. 1 illustrates in color the cultivar (cultivated with pinching) including foliage and flowers.
Figure 2:
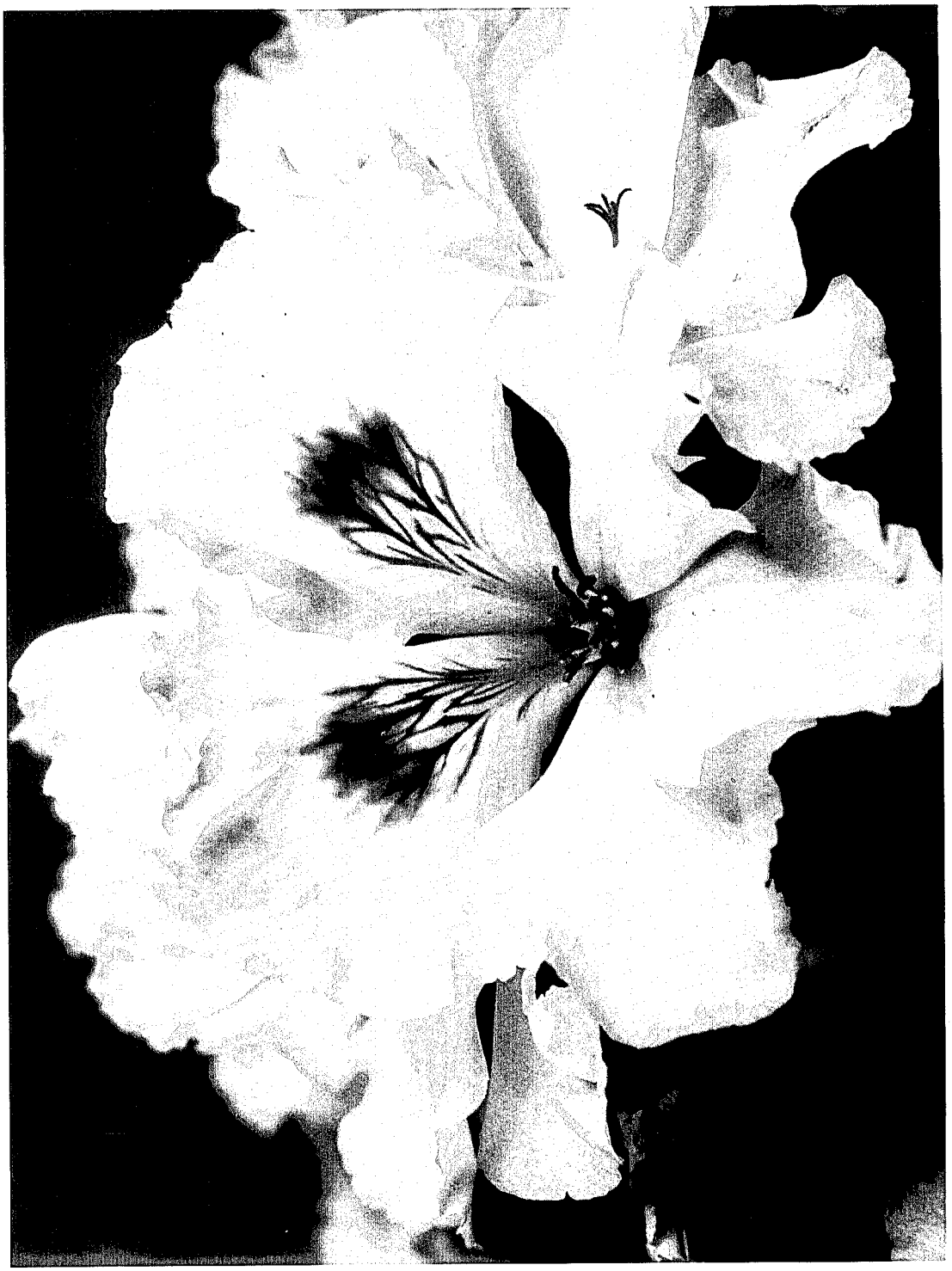
FIG. 2 illustrates in color primarily the floret.

With reference to the detailed description of the cultivar which follows, the test plant was potted in soilless medium and growth in a glasshouse under natural sunlight, at a night temperature of about 58° F. and a day temperature of about 68° F. Fertilizer was applied in every watering, with 200 ppm nitrogen provided in the forms of 15-16-17 (two consecutive waterings) and 20-0-20 (every third watering) in a repeating cycle.

Color readings were taken under incandescent light at approximately 200 foot candles and color identification was by reference to The Royal Horticultural Society Colour Charts, except where common terms of color definition are employed.

THE PLANT

Classification:

*Botanical.*—*Pelargonium*×*domesticum.*

*Tradename.*—#71-(82-23-21)='Crystal'.

Form: Very compact, self-branching.

Height: 13–22 cm [will vary with environmental and cultural conditions].

Leaves:

*Size.*—Largest leaf measured 7.0 cm long×9.5 cm wide.

*Shape.*—Depressed ovate; base is cuneate to truncate to reniform; variously lobed; ratio of length to width is 2 to 3.

*Margin.*—Toothed.

*Texture.*—Pubescent.

*Color.*—Adaxial: Green 137B. Abaxial: Green 138A.

*Ribs and veins.*—Palmate venation.

*Petioles.*—Texture: Lightly pubescent. Length: Up to 7.0 cm. Color: Yellow-green 144A.

Stem:

*Internode length.*—Up to 2.5 cm.

*Color.*—Yellow-green 144A.

THE FLOWER

Blooming habit: Floriferous, early.

Inflorescence form: Umbellate.

Inflorescence size: Varies with floret number; often 8.0–11.0 cm across (with florets fully open).

Disease resistance: Not known.

Florets:

*Number.*—Up to 7 per inflorescence.

*Form.*—Cupped.

*Size.*—5.0–7.0 cm across open floret.

*Lasting quality.*—Excellent, comparable to the cultivar 'Virginia'.

Petals:

*Number.*—5–7.

*Texture and appearance.*—Smooth, with ruffled margins.

*Color.*—Upper petals: Adaxial: White 155D. 1–2 Small central spots: Greyed-purple 185A with slightly broader red 47C halo. Feathering in proximal one-half below spots: Red-Purple 61A. Abaxial: White 155D. Lower petals: Adaxial: White 155D. Abaxial: White 155D.

Petaloids:

*Number.*—0, 1 or 2.

*Shape.*—Petal-like (some are fused to sepals).

*Color.*—Similar to the color of the petals.

Sepals:

*Number.*—5–7.

Pedicel: Subtended by bracts.

*Length.*—2.0–2.7 cm on open floret.

*Color.*—Yellow-green 144A.

Peduncle: Arises from node; opposed to leaf petiole; subtended by leaves and bracts.

*Length.*—Up to 7.5 cm.

*Color.*—Yellow-green 144A.

Reproductive Organs

Androdecium:

*Stamens.*—8–10 flat, ribbon-like filaments, joined at their bases; upper $\frac{1}{3}$ of filaments is light purple; versatile attachment to anthers which are light purple and well developed; 2 sizes of orange pollen.

*Staminodes.*—2–3 flat, ribbon-like filaments with no anthers.

*Petaloid stamens.*—None observed.

Gynoecium:

*Pistil number.*—1.

*Length.*—14.0–24.0 mm.

*Stigma.*—5–7-parted; purple.

*Style.*—8.0–10.5 mm long; purple.

*Ovary.*—6.0–8.0 mm long; superior; very pubescent.

*Fruit.*—Schizocarp; rarely observed.

What is claimed is:

1. A new and distinct cultivar of regal Pelargonium substantially as illustrated and described herein, particularly characterized as being compact and self-branching, early flowering and floriferous, exhibiting excellent postharvest keeping quality, and having white flowers with distinctive red feathering on the upper two petals thereof.

* * * * *